United States Patent
Imai

(10) Patent No.: US 7,332,606 B2
(45) Date of Patent: Feb. 19, 2008

(54) PROCESS FOR PRODUCING 1-BENZYL-4-[(5,6-DIMETHOXY-1-INDANON)-2-YL]METHYLPIPERIDINE OR HYDROCHLORIDE THEREOF

(75) Inventor: Akio Imai, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 7 days.

(21) Appl. No.: 11/546,444

(22) Filed: Oct. 12, 2006

(65) Prior Publication Data

US 2007/0088055 A1   Apr. 19, 2007

Related U.S. Application Data

(60) Provisional application No. 60/730,884, filed on Oct. 28, 2005.

(30) Foreign Application Priority Data

Oct. 14, 2005   (JP) ............................. 2005-299526

(51) Int. Cl.
*C07D 211/02* (2006.01)
*C07D 211/14* (2006.01)

(52) U.S. Cl. ...................................... 546/206; 546/205
(58) Field of Classification Search ................ 546/206, 546/205
See application file for complete search history.

(56) References Cited

FOREIGN PATENT DOCUMENTS

| JP | 64-79151 A | 3/1989 |
|---|---|---|
| JP | 2578475 B2 | 11/1996 |
| JP | 11-171861 A | 6/1999 |
| JP | 2965675 B2 | 8/1999 |

*Primary Examiner*—Charanjit S. Aulakh
(74) *Attorney, Agent, or Firm*—Birch, Stewart, Kolasch & Birch, LLP

(57) ABSTRACT

1-Benzyl-4-[(5,6-dimethoxy-1-indanon)-2-yl]methylpiperidine or hydrochloride thereof, which is useful as a drug, can be produced in high purity by safer and easier operations suitable for industrial production by subjecting 1-benzyl-4-[(5,6-dimethoxy-1-indanon)-2-ylidene]methyl-piperidine or a solvate thereof to catalytic hydrogenation in the presence of a palladium-alumina catalyst and if necessary, converting the thus obtained compound to its hydrochloride.

8 Claims, No Drawings

PROCESS FOR PRODUCING 1-BENZYL-4-[(5,6-DIMETHOXY-1-INDANON)-2-YL]METHYLPIPERIDINE OR HYDROCHLORIDE THEREOF

This Nonprovisional application claims priority under 35 U.S.C. §119(e) on U.S. Provisional Application No. 60/730,884 filed on Oct. 28, 2005, and 35 U.S.C. §119(a) on patent application Ser. No. 2005-299526 filed in Japan on Oct. 14, 2005, the entire contents of which are hereby incorporated by reference.

FIELD OF THE INVENTION

The present invention relates to a process for producing 1-benzyl-4-[(5,6-dimethoxy-1-indanon)-2-yl]methylpiperidine or hydrochloride thereof, which is useful as a drug. The hydrochloride produced by the process of the present invention, i.e., 1-benzyl-4-[(5,6-dimethoxy-1-indanon)-2-yl]methylpiperidine hydrochloride (common name: Donepezil hydrochloride) is effective in the treatment, prevention, remission, amelioration and the like of, for example, various senile dementias such as Alzheimer type senile dementia, etc.; cerebrovascular accidents associated with, for example, a cerebral accident (e.g. cerebral hemorrhage or cerebral infarction), cerebral arteriosclerosis, or an external wound in head; and aprosexia, lalopathy, hypobulia, emotional changes, memory disturbance, hallucinatory-paranoid syndrome and behavioral changes which are associated with, for example, encephalitis or cerebral palsy.

BACKGROUND OF THE INVENTION

1-Benzyl-4-[(5,6-dimethoxy-1-indanon)-2-yl]methylpiperidine of formula (I) (hereafter referred to as the compound of formula (I) or Donepezil)

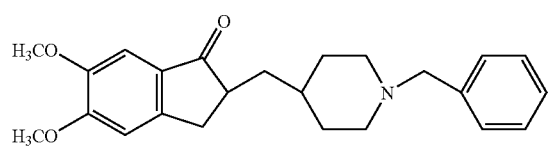

(I)

is a well-known compound, and is known to be producible by catalytic hydrogenation of 1-benzyl-4-[(5,6-dimethoxy-1-indanon)-2-ylidene]methylpiperidine of formula (II) (hereinafter referred to as the compound of formula (II)) (see, for example, JP-A-1-79151, Japanese Patent No. 2578475 and Japanese Patent No. 2965675).

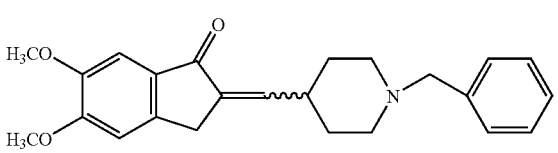

(II)

JP-A-1-79151 discloses, at page 15, the right lower column and page 17, the left upper column, a reaction scheme represented by the following formulas:

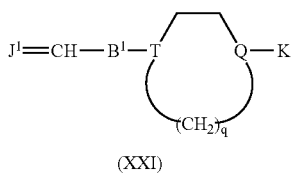

(XXI)

↓ reduction

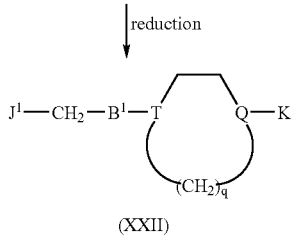

(XXII)

JP-A-1-79151 discloses, at page 16, the left upper, lines 11 to 13, a process of producing a compound of general formula (XXII) by catalytic hydrogenation of a compound of general formula (XXI) by the use of palladium-carbon, Raney nickel or rhodium-carbon.

Furthermore, in Example 4 of JP-A-1-79151, hydrogenation in tetrahydrofuran as solvent for reaction in the presence of 10% palladium-carbon at ordinary temperature and atmospheric pressure is described as an example of reaction.

Japanese Patent No. 2578475 discloses, at pages 3 to 4, a reaction scheme represented by the following formulas:

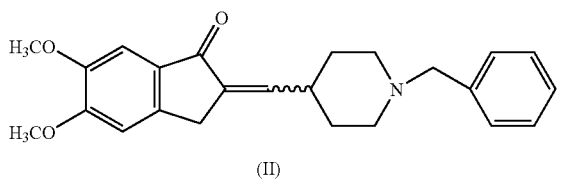

(II)

↓ reduction

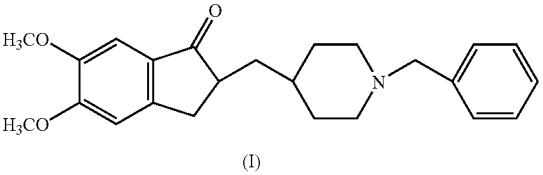

(I)

Japanese Patent No. 2578475 discloses, at page 3, the right column, line 3 from the bottom to the last line, a process of producing the compound of formula (I) by reduction of the compound of formula (II) and describes the fact that when catalytic reduction is carried out, employment of, for example, palladium-carbon, Raney nickel or rhodium-carbon brings about a desirable result. In Example 1 of Japanese Patent No. 2578475, hydrogenation in tetrahydrofuran as solvent for reaction in the presence of 10% palladium-carbon at ordinary temperature and atmospheric pressure is described as an example of reaction.

Japanese Patent No. 2965675 discloses, at page 4, a reaction scheme represented by the following formulas:

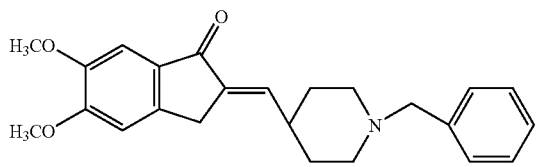

(II')

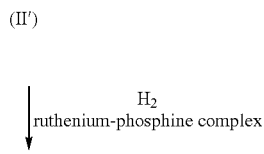

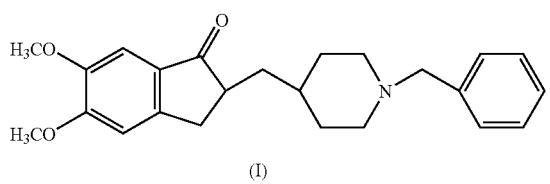

(I)

Japanese Patent No. 2965675 describes, at page 6, the left column, lines 5 to 19, as follows: a mixture of a compound of formula (II') and a ruthenium-phosphine complex is dissolved in a solvent such as methylene chloride and the reaction is preferably carried out in an autoclave under the following conditions: hydrogen pressure 4 to 100 kg/cm², reaction temperature 25 to 75° C., and reaction time 24 to 168 hours. In Example 1 of Japanese Patent No. 2965675, the compound of formula (II') is reacted in methylene chloride in the presence of a complex [Ru$_2$Cl$_2$((S)-(−)-BINAP)$_2$N(C$_2$H$_5$)$_3$] at a hydrogen pressure of 77 kg/cm² at 50° C. for 30 minutes and then at room temperature for 140 hours.

BRIEF SUMMARY OF THE INVENTION

JP-A-1-79151 and Japanese Patent No. 2578475 disclose in working examples that the compound of formula (II) is converted to the compound of formula (I) by catalytic hydrogenation using 10% palladium-carbon as a catalyst. In this case, since the selectivity of the reaction is insufficient, the reaction product should be purified by column chromatography. In Japanese Patent No. 2965675, the production of an optically active compound of formula (I) by asymmetric hydrogenation is aimed at, but because of employment of a homogeneous catalyst, at least a separation procedure and the like are necessary for removing the catalyst. Therefore, such a production process is disadvantageous in time and cost as an industrial production process. Accordingly, there has been a desire for a production process of the compound of formula (I) or a salt thereof which comprises easy operations and is suitable for industrial production.

The present inventors earnestly investigated in order to solve the problems described above, and consequently found a simpler process for producing the compound of formula (I) or hydrochloride thereof in high purity by catalytic hydrogenation of the compound of formula (II) or a solvate thereof in the presence of a palladium-alumina catalyst.

Generally, in catalytic hydrogenation, attention should be paid to side reactions in the case of a compound having many functional groups. The compound of formula (II):

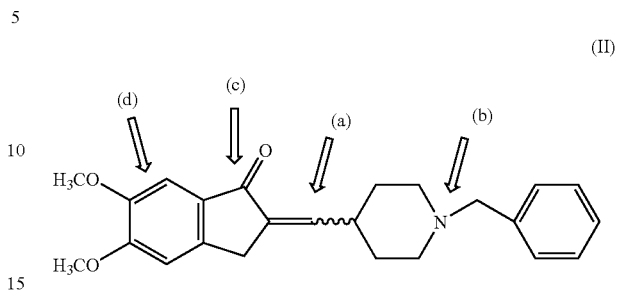

(II)

has reaction sites (a) to (d), and the desired compound of formula (I) can be obtained by selective hydrogenation only in the reaction site (a). When the compound of formula (II) is subjected to catalytic hydrogenation using a commonly used catalyst, hydrogenolysis proceeds at the same time particularly in the reaction site (b) to give a by-product (a debenzylated product) represented by formula (III):

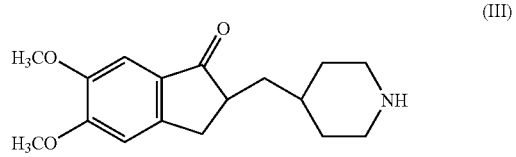

(III)

Therefore, there is a problem of a yield decrease and a well-known purifying method such as column chromatography or recrystallization is considered necessary. Moreover, when the catalyst and the reaction conditions are chosen, attention should be paid also to the reduction of the carbonyl group in the reaction site (c) and the hydrogenation of the benzene ring in the reaction site (d). The present inventors found that the side reactions such as the hydrogenolysis can be prevented by using a palladium-alumina catalyst and choosing the reaction conditions, so that the compound of formula (I) or a salt thereof can be obtained in high purity and yield. Thus, a production process suitable for industrially producing the compound of formula (I) or hydrochloride thereof more easily in higher yield has been completed.

The present invention relates to a process for producing 1-benzyl-4-[(5,6-dimethoxy-1-indanon)-2-yl]methyl-piperidine of formula (I):

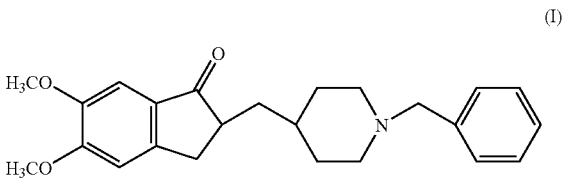

(I)

or hydrochloride thereof, which comprises:

Step P1: converting 1-benzyl-4-[(5,6-dimethoxy-1-indanon)-2-ylidene]methyl-piperidine of formula (II):

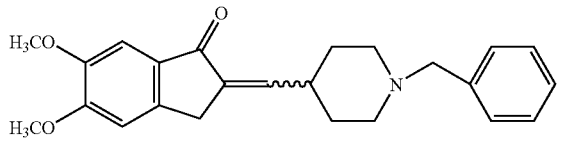

(II)

or a solvate thereof to the compound of formula (I) by catalytic hydrogenation in the presence of a palladium-alumina catalyst; and Step P2: if necessary, converting the obtained compound of formula (I) to its hydrochloride after or without isolation of the compound.

The production process of the present invention preferably comprises the Step (P1).

In the production process of the present invention, a solvent for reaction used in the catalytic hydrogenation is preferably methanol, tetrahydrofuran, toluene, ethyl acetate, or a mixture thereof.

In the production process of the present invention, the reaction temperature for the catalytic hydrogenation is preferably 0 to 25° C.

In the production process of the present invention, the hydrogen pressure in the catalytic hydrogenation is preferably 0.1 to 2 Megapascal (MPa).

DETAILED DESCRIPTION OF THE INVENTION

The process for producing the compound of formula (I) or hydrochloride thereof of the present invention is explained below in detail.

The compound of formula (I) or hydrochloride thereof can be produced by subjecting the compound of formula (II) or a solvate thereof to catalytic hydrogenation in the presence of a palladium-alumina catalyst, and if necessary, forming the hydrochloride.

The compound of formula (II) is well known and can be produced, for example, by the process described in JP-A-1-79151, Japanese Patent No. 2578475 or JP-A-11-171861.

The term "solvate" means a compound formed by the incorporation of a solvent used for crystallization into the crystal lattice of the compound of formula (II) in a definite proportion in the production of this compound. The solvate includes, for example, hydrate, solvate with methanol, solvate with ethanol, and solvate with toluene. The solvate can be used in the catalytic hydrogenation reaction as it is so long as it does not inhibit the reaction. Similarly, the compound of formula (II) can be used as it is without a particular drying procedure so long as a solvent used for crystallizing the compound or a solvent used for washing in filtration for the production of the compound does not inhibit the catalytic hydrogenation reaction.

The palladium-alumina catalyst is not particularly limited and an example thereof is alumina powder supporting palladium thereon in an amount of 1 to 10% by weight. For example, 1% by weight palladium-alumina (20, 570-2), 5% by weight palladium-alumina (20, 571-0) and 10% by weight palladium-alumina (44, 008-6) are available by Aldrich, and they can be used as they are.

As to the amount of the palladium-alumina catalyst used, the palladium-alumina catalyst is preferably used in an amount of 1 to 20% by weight based on the weight of the compound of formula (II), i.e., the starting material.

The solvent for reaction used is not particularly limited so long as it does not inhibit the reaction. For example, methanol, tetrahydrofuran, toluene, ethyl acetate, or a mixture thereof is preferably used as the solvent for reaction.

The hydrogen pressure in the catalytic hydrogenation is not particularly limited and is preferably, for example, 0.1 to 2 MPa, more preferably 0.1 to 1 MPa.

Although the reaction temperature is not particularly limited, the reaction is carried out, for example, at 0 to 25° C., preferably 0 to 15° C., more preferably 2 to 10° C. The reaction is usually completed in 30 minutes to 10 hours, preferably 50 minutes to 5 hours.

The hydrochloride can be formed from a solution of the compound of formula (I) in a solvent by a conventional method of hydrochloride formation, such as bubbling of hydrogen chloride gas into the solution, addition of a solution prepared by previous dissolution of hydrogen chloride in a solvent, or addition of hydrochloric acid. As the solution of the compound of formula (I), a solution obtained by removing the catalyst by filtration of the reaction solution for the catalytic hydrogenation is used as it is, or there is used a solution with a higher concentration prepared by concentrating a part of the catalyst-free solution, or a solution prepared by concentrating the catalyst-free solution and then dissolving the concentrate in a different solvent. Alternatively, the solution of the compound of formula (I) is obtained by isolating the compound of formula (I) by crystallization or the like and dissolving the isolated compound in a solvent.

The solvent used for forming the hydrochloride is not particularly limited so long as it does not inhibit the conversion to the hydrochloride or the crystallization of the hydrochloride. As the solvent, ethanol, tetrahydrofuran or ethyl acetate is preferably used.

It is also possible to convert the hydrochloride formed to the free compound of formula (I) as follows. The hydrochloride is dissolved in a mixed solvent of water and ethanol and the resulting solution is adjusted to pH 8 to 14, preferably pH 9 to 12, with a base (e.g. sodium hydroxide or sodium carbonate) or an aqueous solution thereof, and the compound of formula (I) thus precipitated is collected by filtration or extracted with an organic solvent such as ethyl acetate, tetrahydrofuran or toluene.

The production process of the present invention is characterized in that in the production of the compound of formula (I) by catalytic hydrogenation of the compound of formula (II), the production of the compound of formula (III) (the debenzylated product) produced as a by-product by hydrogenolysis, a side reaction is suppressed.

In Examples 1 to 6 as typical examples of the present invention, the purity of the compound of formula (I) and the content of the compound of formula (III) in the reaction solution were measured by HPLC analysis under the following conditions and compared with those measured in Reference Examples 1 and 2 using the same palladium-carbon as used in JP-A-1-79151 and Japanese Patent No. 2578475. The results obtained are shown in Table 1.

HPLC Conditions
Detector: an ultraviolet absorptiometer
(detecting
wavelength: 271 nm)
Column: Inertsil ODS-2, 4.6 mmφ×150 mm Mobile phase: acetonitrile:water:
perchloric acid
(70%): sodium 1-decanesulfonate=350 ml: 650 ml:1 ml:2.5 g
Flow rate: 1.4 ml/min
Column temperature: 35° C.
Sample: Donepezil hydrochloride 10 mg/mobile
phase 25 ml
Injecting volume: 20 μl
The reaction solution is injected after proper dilution (for example, about 500-fold dilution, injected in a volume of 10 μl).

TABLE 1

| Test sample | Compound (I) content (%) | Compound (III) content (%) |
|---|---|---|
| Example 1 | 99.0 | 0.7 |
| Example 2 | 99.4 | 0.4 |
| Example 3 | 99.2 | 0.8 |
| Example 4 | 99.3 | 0.7 |
| Example 5 | 98.4 | 1.5 |
| Example 6 | 98.4 | 0.9 |
| Comparative Example 1 | 62.5 (starting material 34.8) | 2.6 |
| Comparative Example 2 | 72.9 (starting material 25.3) | 1.8 |

As is clear from the results shown in Table 1, the present invention makes it possible to produce the compound of formula (I) or hydrochloride thereof in higher purity. That is, the present invention permits omission of the purification procedure (e.g. column chromatography) required in patent document 1 or patent document 2 and hence makes it possible to produce the compound of formula (I) more easily in higher yield.

According to the present invention, the compound of formula (I) or hydrochloride thereof can be industrially produced more easily in higher yield.

The present invention is illustrated in detail with reference to the following examples, which should not be construed as limiting the scope of the invention.

EXAMPLE 1

To 200 ml of tetrahydrofuran were added 20 g of 1-benzyl-4-[(5,6-dimethoxy-1-indanon)-2-ylidene]methyl-piperidine and 2 g of 5% palladium-alumina. Hydrogenation was carried out with stirring for 5 hours at a pressure of 0.4 to 0.8 MPa and a temperature of 3 to 4° C.

After completion of the hydrogenation, the reaction solution was freed from the catalyst and then concentrated. After 160 mL of ethanol was added to the concentration residue to obtain a solution, 6.0 g of concentrated hydrochloric acid was added thereto with stirring to carry out conversion to hydrochloride. The crystallized hydrochloride was collected by filtration and dried to obtain 19.8 g of Donepezil hydrochloride.

HPLC purity: the reaction solution/99.0%, the hydrochloride/99.9%.

The values of $^1$H-NMR were identified with those of Example 3.

EXAMPLE 2

To 200 mL of tetrahydrofuran were added 20 g of 1-benzyl-4-[(5,6-dimethoxy-1-indanon)-2-ylidene]methyl-piperidine and 2 g of 5% palladium-alumina. Hydrogenation was carried out with stirring for 3 hours at a pressure of 0.5 to 0.8 MPa and a temperature of 4 to 5° C.

After completion of the hydrogenation, the reaction solution was freed from the catalyst and then concentrated. After 160 mL of ethanol was added to the concentration residue to obtain a solution, 6.0 g of concentrated hydrochloric acid was added thereto with stirring to carry out conversion to hydrochloride. The crystallized hydrochloride was collected by filtration and dried to obtain 20.6 g of Donepezil hydrochloride, i.e., hydrochloride of the compound of formula (I).

HPLC Purity: the reaction solution/99.4%, the hydrochloride/99.9%.

The values of $^1$H-NMR were identified with those of Example 3.

EXAMPLE 3

To 913 mL of tetrahydrofuran were added 91.3 g of 1-benzyl-4-[(5,6-dimethoxy-1-indanon)-2-ylidene]methyl-piperidine and 9 g of 5% palladium-alumina. Hydrogenation was carried out with stirring for 4 hours at a pressure of 0.4 to 1.0 MPa and a temperature of 3 to 6° C.

After completion of the hydrogenation, the reaction solution was freed from the catalyst and then concentrated. After 730 mL of ethanol was added to the concentration residue to obtain a solution, 27.5 g of concentrated hydrochloric acid was added thereto with stirring to carry out conversion to hydrochloride. The crystallized hydrochloride was collected by filtration and dried to obtain 95.1 g of Donepezil hydrochloride.

HPLC Purity: the reaction solution/99.2%, the hydrochloride/99.8%.

The values obtained by $^1$H-NMR were as follows:
$^1$H-NMR (400 MHz, CD$_3$OD) δ (ppm): 1.35-1.60 (3H, m), 1.75-2.12 (4H, m), 2.68-2.77 (2H, m), 3.04 (2H, br.s), 3.27-3.35 (1H, m), 3.49 (2H, br.s), 3.84 (3H, s), 3.94 (3H, s), 4.32 (2H, s), 7.05 (1H, s), 7.13 (1H, s), 7.47-7.55 (5H, m)

EXAMPLE 4

To 500 mL of tetrahydrofuran were added 50 g of 1-benzyl-4-[(5,6-dimethoxy-1-indanon)-2-ylidene]methyl-piperidine and 5 g of 5% palladium-alumina. Hydrogenation was carried out with stirring for 50 minutes at a pressure of 0.5 to 1.0 MPa and a temperature of 14 to 20° C.

After completion of the hydrogenation, the catalyst was removed and then a part of the solvent in the reaction solution was removed by distillation and concentration. To the residual reaction solution after the removal by distillation and concentration was added 15 g of concentrated hydrochloric acid with stirring to carry out conversion to hydrochloride. The crystallized hydrochloride was collected by filtration and dried to obtain 52.6 g of Donepezil hydrochloride, i.e., hydrochloride of the compound of formula (I).

HPLC Purity: the reaction solution/99.3%, the hydrochloride/99.5%.

The values of $^1$H-NMR were identified with those of Example 3.

EXAMPLE 5

To 500 mL of toluene were added 50 g of 1-benzyl-4-[(5,6-dimethoxy-1-indanon)-2-ylidene]methyl-piperidine and 5 g of 5% palladium-alumina. Hydrogenation was carried out with stirring for 3 hours at a pressure of 0.2 to 0.5 MPa and a temperature of 9 to 12° C.

After completion of the hydrogenation, the reaction solution was freed from the catalyst and then concentrated. After 400 mL of ethanol was added to the concentration residue to obtain a solution, 15 g of concentrated hydrochloric acid was added thereto with stirring to carry out conversion to hydrochloride. The crystallized hydrochloride was collected by filtration and dried to obtain 48.8 g of Donepezil hydrochloride.

HPLC Purity: the reaction solution/98.4%, the hydrochloride/99.4%.

The values of $^1$H-NMR were identified with those of Example 3.

EXAMPLE 6

To 500 mL of toluene were added 50 g of 1-benzyl-4-[(5,6-dimethoxy-1-indanon)-2-ylidene]methyl-piperidine and 5 g of 5% palladium-alumina. Hydrogenation was carried out with stirring for 2 hours and 20 minutes at a pressure of 0.4 to 0.8 MPa and a temperature of 10 to 11° C.

After completion of the hydrogenation, the reaction solution was freed from the catalyst and then concentrated. After 400 mL of ethanol was added to the concentration residue to obtain a solution, 15 g of concentrated hydrochloric acid was added thereto with stirring to carry out conversion to hydrochloride. The crystallized hydrochloride was collected by filtration and dried to obtain 45.2 g of Donepezil hydrochloride.

HPLC Purity: the reaction solution/98.4%, the hydrochloride/99.2%.

The values of $^1$H-NMR were identified with those of Example 3.

REFERENCE EXAMPLE 1

To 8 mL of tetrahydrofuran were added 1 g of 1-benzyl-4-[(5,6-dimethoxy-1-indanon)-2-ylidene]methyl-piperidine and 0.2 g of 10% palladium-carbon. Hydrogenation was carried out with stirring for 1.5 hours at 0 to 2° C. and atmospheric pressure.

HPLC Purity of the Reaction Solution: the desired compound/62.5%, the starting material/34.8%, the debenzylated product/2.6%.

REFERENCE EXAMPLE 2

To 200 mL of toluene were added 20 g of 1-benzyl-4-[(5,6-dimethoxy-1-indanon)-2-ylidene]methyl-piperidine and 2 g of 10% palladium-carbon. Hydrogenation was carried out with stirring for 5 hours at 0 to 1° C. and 0.8 to 1.0 MPa.

HPLC Purity of the Reaction Solution: the desired compound/72.9%, the starting material/25.3%, the debenzylated product/1.8%.

According to the present invention, the compound of formula (I) or hydrochloride thereof (Donepezil hydrochloride) can be industrially produced more easily in higher yield.

What is claimed is:

1. A process for producing 1-benzyl-4-[(5,6-dimethoxy-1-indanon)-2-yl]methyl-piperidine) of formula (I):

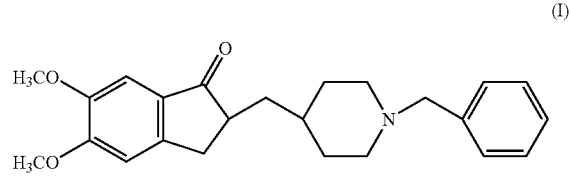

or hydrochloride thereof, which comprises:

Step P1: converting 1-benzyl-4-[(5,6-dimethoxy-1-indanon)-2-ylidene]methyl-piperidine of formula (II):

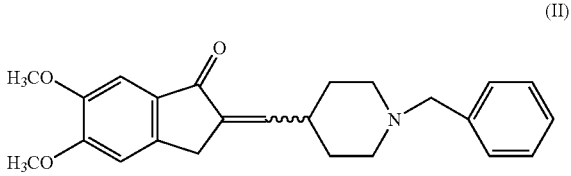

or a solvate thereof to the compound of formula (I) by catalytic hydrogenation in the presence of a palladium-alumina catalyst; and Step P2: if necessary, converting the obtained compound of formula (I) to its hydrochloride after or without isolation of the compound.

2. A process for producing hydrochloride of the compound of formula (I) according to claim 1, which comprises the Step (P2).

3. A process according to claim 1 or 2, wherein a solvent for reaction used in the catalytic hydrogenation is methanol, tetrahydrofuran, toluene, ethyl acetate, or a mixture thereof.

4. A process according to claim 1 or 2, wherein the reaction temperature for the catalytic hydrogenation is 0 to 25° C.

5. A process according to claim 1 or 2, wherein the hydrogen pressure in the catalytic hydrogenation is 0.1 to 2 MPa.

6. A process according to claim 3, wherein the reaction temperature for the catalytic hydrogenation is 0 to 25° C.

7. A process according to claim 3, wherein the hydrogen pressure in the catalytic hydrogenation is 0.1 to 2 MPa.

8. A process according to claim 4, wherein the hydrogen pressure in the catalytic hydrogenation is 0.1 to 2 MPa.

* * * * *